(12) United States Patent
Lu et al.

(10) Patent No.: US 8,753,624 B2
(45) Date of Patent: Jun. 17, 2014

(54) **COMPOSITION AND USE OF *LACTOBACILLUS PARACASEI* STRAIN GMNL-133 IN TREATING ATOPIC DERMATITIS OR OTHER ALLERGIC DISEASES**

(75) Inventors: Ying-Chen Lu, Chiayi (TW); Feng-Ching Hsieh, Pingtung County (TW)

(73) Assignee: GenMont Biotech Incorporation, Tainan (TW)

( * ) Notice: Subject to any disclaimer, the term of this patent is extended or adjusted under 35 U.S.C. 154(b) by 116 days.

(21) Appl. No.: 13/273,228

(22) Filed: Oct. 14, 2011

(65) Prior Publication Data

US 2013/0095086 A1 Apr. 18, 2013

(51) Int. Cl.
*A01N 63/00* (2006.01)
(52) U.S. Cl.
USPC ........................................ 424/93.44; 424/93.1
(58) Field of Classification Search
USPC ............................................. 424/93.44, 93.1
See application file for complete search history.

(56) References Cited

U.S. PATENT DOCUMENTS 8,361,481 B2 * 1/2013 Hara et al. ................. 424/234.1

FOREIGN PATENT DOCUMENTS

| CN | 101575582 A | 11/2009 |
| TW | I284149 | 10/2005 |
| WO | 2009131208 A1 | 10/2009 |

OTHER PUBLICATIONS

Kaplan et al. (Variation between observed and true Terminal Restriction Fragment length is dependent on true TRF length and purine content. J. Microbiol. Methods (2003) 54 (1), 121-125).*
Altman H. et al.:"In vitro assessment of antimicrobial peptides as potential agents against several oral bacteria" 2006.
Rosenfeldt V et al:"Effect of Probiotic *Lactobacillus* Strains in Children With Atopic Dermatitis" 2003.

* cited by examiner

*Primary Examiner* — Karen Cochrane Carlson
*Assistant Examiner* — Natalie Moss
(74) *Attorney, Agent, or Firm* — CKC & Partners Co., Ltd.

(57) ABSTRACT

An isolated *Lactobacillus paracasei* strain GMNL-133 is disclosed, which was deposited in the China Center for Type Culture Collection (CCTCC) under the accession number of CCTCC M 2011331 is disclosed. The isolated *Lactobacillus paracasei* strain GMNL-133 is used for preparing a composition for use in the treatment of atopic dermatitis or other allergic diseases in an effective amount. And a composition for use in the treatment of atopic dermatitis or other allergic diseases comprises an effective amount of the *Lactobacillus paracasei* strain GMNL-133 is also disclosed.

5 Claims, 8 Drawing Sheets

SEQUENCE LISTING

<160> NUMBER OF SEQ ID NOS: 2

<210> SEQ ID NO 1
<211> LENGTH: 507
<212> TYPE: DNA
<213> ORGANISM: Lactobacillus paracasei
<220> FEATURE:
<223> OTHER INFORMATION: 16S rDNA partial gene sequence of Lactobacillus paracas GMNL-133

<400> SEQUENCE: 1

```
ggctcaggat gaacgctggc ggcgtgccta atacatgcaa gtcgaacgag            50
ttctcgttga tgatcggtgc ttgcaccgag attcaacatg gaacgagtgg           100
cggacgggtg agtaacacgt gggtaacctg cccttaagtg ggggataaca           150
tttggaaaca gatgctaata ccgcatagat ccaagaaccg catggttctt           200
ggctgaaaga tggcgtaagc tatcgctttt ggatggaccc gcggcgtatt           250
agctagttgg tgaggtaayg gctcaccaag gcgatgatac gtagccgaac           300
tgagaggttg atcggccaca ttgggactga gacacgccc aaactcctac            350 gggaggcagc agtagggaat cttccacaat ggacgcaagt ctgatggagc           400
aacgccgcgt gagtgaagaa ggctttcggg tcgtaaaact ctgttgttgg           450
agaagaatgg tcggcagagt aactgttgtc ggcgtgacgg tatccaacca           500
gaaagcc                                                          507
```

<210> SEQ ID NO 2
<211> LENGTH: 10
<212> TYPE: DNA
<213> ORGANISM: Artificial Sequence
<220> FEATURE:
<223> OTHER INFORMATION: Primer sequence for RAPD PCR analysis of gene of Lactobacillus paracasei

<400> SEQUENCE: 2

```
ccgcgacgtt                                                        10
```

COMPOSITION AND USE OF *LACTOBACILLUS PARACASEI* STRAIN GMNL-133 IN TREATING ATOPIC DERMATITIS OR OTHER ALLERGIC DISEASES

SEQUENCE LISTING

The sequence listing submitted via EFS, in compliance with 37 CFR §1.52(e)(5), is incorporated herein by reference. The sequence listing text file submitted via EFS contains the file "TWT01968US-SeqListing.txt", created on Oct. 14, 2011, which is 1,356 bytes in size.

BACKGROUND

1. Field of Invention

The present invention relates to a *Lactobacillus* sp. strain and the use thereof. More particularly, the present invention relates to a *Lactobacillus paracasei* strain and an oral composition containing thereof for use in the treatment of allergic disease.

2. Description of Related Art

Allergy refers to an acquired potential to develop immunologically mediated adverse reaction to normally innocuous substances. Allergic reaction provokes symptoms such as itching, coughing, wheezing, sneezing, watery eyes, inflammation and fatigue. It is normally believed that allergic reaction includes an early specific immune response and a late inflammatory reaction. It is reported that allergens (e.g., pollens and mite dust) mediate the early allergic response by stimulating high affinity immunoglobulin E (IgE) receptors. For instance, mast cells and basophils stimulated by allergens will release histamine and cytokines. Then the cytokines released from mast cells and basophils mediate the late allergic response by recruiting inflammatory cells. It is also reported that the influx of eosinophils, macrophages, lymphocytes, neutrophils and platelets starts the late vicious inflammatory cycle. This late inflammatory cycle amplifies the early immune response and triggers more inflammatory cells release.

Various therapies have been used to treat the symptoms of allergies, such as anti-allergic and histamine H-receptor antagonists (anti-histamines). Anti-histamines can reduce the redness, itching and swelling caused by the histamine reacting on the target tissues and prevent and alleviate many symptoms resulting from the degranulation of mast cells. However, anti-histamines have also been associated with side effects such as diminished alertness, slowed reaction times and somnolence.

Atopic dermatitis is one of the most common allergic diseases in children. The conventional method for treating atopic dermatitis is topic steroid therapy. However, symptoms of atopic dermatitis are difficult to eradicate and recur frequently after stopping steroids administration. Furthermore, long-term use of steroid is prone to side effects such as skin atrophy and thinning, changes in skin pigmentation, hair growing, and acne. Therefore, less side effects and highly safety therapy is required.

In recent years, probiotics has been considered that help human health and no side effects by the medical community and the scientific community. According to the currently adopted definition by Food and Agriculture organization of the United Nations (FAO) and World Health Organization (WHO), probiotics are: "Live microorganisms which when administered in adequate amounts confer a health benefit on the host". Currently, there are many microorganisms can be used as probiotics such as *Lactobacillus* sp., *Bifidobacterium* sp., *Lactococcus* sp., *Enterococcus* sp., yeasts and *Streptococcus* sp.

Lactic acid bacteria is a group of gram-positive facultative anaerobic bacteria, which is commonly found in the human gastrointestinal tract and vagina, and can ferment sugar to lactic acid as major metabolites. There are many studies and clinical trials are gradually confirmed that an important correlation between lactic acid bacteria and human health. At present, the lactic acid bacteria have been found that has many effects such as improving the balance of intestinal microflora, diarrhea prevention, reducing colon cancer risk, stimulating the normal development and function of gastrointestinal epithelial mucosal system, producing several vitamins and nutrients, and prevention and treatment of vaginosis.

SUMMARY

An isolated *Lactobacillus paracasei* strain GMNL-133 is provided and deposited at the China Center for Type Culture Collection under the accession number of CCTCC M 2011331. According to a preferred embodiment of the present invention the isolated *Lactobacillus paracasei* strain GMNL-133 is for use as a food or a medicament, and still more preferably for the treatment of an allergic disease.

A method for treating an allergic disease in a subject is provided. The method includes the step of administering an isolated *Lactobacillus paracasei* strain GMNL-133 to the subject in a therapeutically effective amount. The isolated *Lactobacillus paracasei* strain GMNL-133 is deposited at the China Center for Type Culture Collection under the accession number of CCTCC M 2011331.

In an embodiment, the isolated *Lactobacillus paracasei* strain GMNL-133 is live.

In another embodiment, the allergic disease is atopic dermatitis.

An oral composition for use in the treatment of allergic disease is provided. The composition includes a therapeutically effective amount of an isolated *Lactobacillus paracasei* strain GMNL-133, which is deposited at the China Center for Type Culture Collection under the accession number of CCTCC M 2011331.

In an embodiment, the isolated *Lactobacillus paracasei* strain GMNL-133 is live.

In another embodiment, the allergic disease is atopic dermatitis.

In a further embodiment, the oral composition also includes an another microorganism strain selected from the group consisting of *Lactobacillus acidophilus*, *Lactobacillus plantarum*, *Bifidobacterium longum*, *Lactobacillus fermentum*, *Lactobacillus bulgaricus*, *Streptococcus thermophilus*, *Lactobacillus cremors*, *Lactobacillus rhamnosus*, *Lactobacillus reuteri* and any combination thereof.

BRIEF DESCRIPTION OF THE DRAWINGS

The invention can be more fully understood by reading the following detailed description of the embodiment, with reference made to the accompanying drawings as follows.

DETAILED DESCRIPTION

Until now, some reports showed that allergy can be treated by regulating cytokines. For example, interferon-γ (IFN-γ) can inhibit cytokines over-expression in type-2 T helper (Th2) cells. IFN-γ especially inhibits IL-4 secretion to lower B cells proliferation. Furthermore, IFN-γ can stimulate the immune response of type-a T helper (Th1) cells and repress the synthesis of IgE. Therefore, it is believed that IFN-γ is effective in treating allergy.

Accordingly, the present invention provides a novel isolated *Lactobacillus paracasei* strain GMNL-133, which can stimulate mice splenocytes to secrete IFN-γ. The novel isolated *Lactobacillus paracasei* strain GMNL-133 can be used for preparing a oral composition for use as a food or a medicament, and in particular for the treatment of allergic diseases. The novel isolated *Lactobacillus paracasei* strain GMNL-133 was deposited at the China Center for Type Culture Collection (CCTCC, Wuhan University, Wuhan 430072, People's Republic of China) under the accession number of CCTCC M 2011331 on Sep. 26, 2011. Together with the isolated *Lactobacillus paracasei* strain GMNL-133 the oral composition comprises at least one pharmaceutically acceptable excipient and/or diluent. Suitable excipients and diluents may further include other ingredients, for example, glucose, maltodextrin, baby milk, fructo-oligosaccharides, magnesium stearate, yogurt spices, other uncertain remains unseparated therefrom or any combination thereof, as well as formulation techniques for preparing the oral composition, are known to a person skilled in the art. Preferably the oral composition comprises a dosage of $10^6$ to $10^{11}$ colony forming units (cfu) of the isolated *Lactobacillus paracasei* strain GMNL-133 per gram.

The term "allergic disease" described herein refers to atopic dermatitis, allergic rhinitis and asthma, and some allergy caused by certain food and insect biting. These diseases lead to a considerable degree of inflammation, resulting in chronic inflammation of skin, mucosa or vascular.

According to an embodiment, there is one single step of orally administrating a therapeutically effective amount of an isolated *Lactobacillus paracasei* strain GMNL-133, deposited at CCTCC under the accession number of CCTCC M 2011331, into a subject included in a method for treating an allergic disease in a subject. The foregoing isolated *Lactobacillus paracasei* strain GMNL-133 is live bacteria or dead bacteria by heat killed process. The foregoing allergic disease is atopic dermatitis.

The present invention also provides an oral composition for use in the treatment of allergic disease. The oral composition includes a therapeutically effective amount of an isolated *Lactobacillus paracasei* strain GMNL-133, which is deposited at the China Center for Type Culture Collection under the accession number of CCTCC M 2011331.

The foregoing isolated *Lactobacillus paracasei* strain GMNL-133 is live bacteria or dead bacteria by heat killed process. The foregoing allergic disease is atopic dermatitis.

According to an embodiment, the oral composition also includes an another microorganism strain selected from the group consisting of *Lactobacillus acidophilus, Lactobacillus plantarum, Bifidobacterium longum, Lactobacillus fermentum, Lactobacillus bulgaricus, Streptococcus thermophilus, Lactobacillus cremors, Lactobacillus rhamnosus, Lactobacillus reuteri* and any combination thereof. The another microorganism strain may have a dosage of $10^7$ CFU per gram or more.

Thereinafter, various applications of the *Lactobacillus paracasei* strain GMNL-133 of the present invention will be described in more details referring to several exemplary embodiments below, while not intended to be limiting. Thus, one skilled in the art can easily ascertain the essential characteristics of the present invention and, without departing from the spirit and scope thereof, can make various changes and modifications of the invention to adapt it to various usages and conditions.

Example 1

Isolation, Selection, and Identification of *Lactobacillus* sp. Strain

Applicant obtained specimens from gastrointestinal tracts of a number of healthy adults. Over 100 isolated strains of *Lactobacillus* sp. were screened from the specimens. In order to search for *Lactobacillus* sp. that has potential in treating allergic disease, the isolated strains were respectively co-cultured with mice splenocytes for analyzing the IFN-γ secretion from the mice splenocytes. It was found that an isolated strain GMNL-133 could stimulate mice splenocytes to secrete more IFN-γ.

Figure 1:
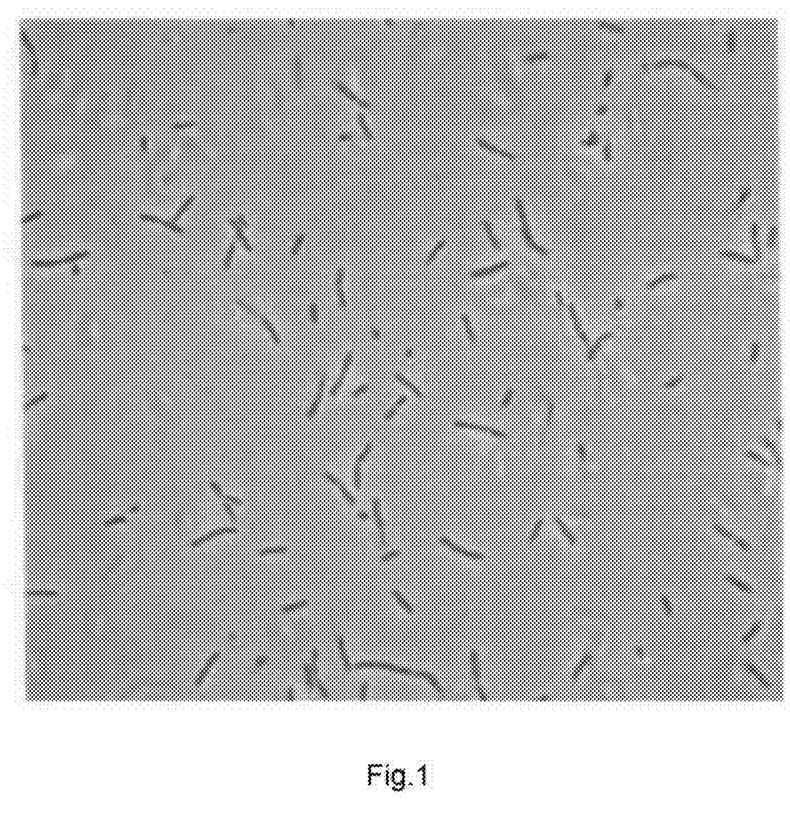
FIG. 1 depicts a microscopic view of the isolated strain GMNL-133 according to an embodiment of the present invention.

The isolated strain GMNL-133 was identified by several bacterial analyses. FIG. 1 depicts a microscopic view of the isolated strain GMNL-133 according to an embodiment of the present invention. The isolated strain GMNL-133 was identified as a gram-positive bacillus bacterium, non-motile, catalase-negative, oxidase-negative, and could grow under both aerobic and anaerobic conditions.

The isolated strain GMNL-133 was further analyzed by 16S rDNA sequence analysis and API 50 CHL metabolic profile. The 16S rDNA partial sequence of the isolated strain GMNL-133 is shown as SEQ ID No. 1. The API 50 CHL metabolic profile of the isolated strain GMNL-133 is listed in Table 1, compared with the standard *Lactobacillus paracasei* subsp. *paracasei* BCRC 12248 and *Lactobacillus paracasei* subsp. *tolerans* BCRC 14628.

TABLE 1

| API Test | GMNL-133 | *Lactobacillus paracasei* subsp. *paracasei* BCRC 12248 | *Lactobacillus paracasei* subsp. *tolerans* BCRC 14628 |
| --- | --- | --- | --- |
| Glycerol | − | − | − |
| Erythritol | − | − | − |
| D-Arabinose | − | − | − |
| L-Arabinose | − | − | − |
| D-Ribose | + | + | − |
| D-Xylose | − | − | − |
| L-Xylose | − | − | − |
| D-Adonitol | − | − | − |
| Methyl-βD-xyloside | − | − | − |
| D-Galactose | + | + | + |
| D-Glucose | + | + | + |
| D-Fructose | + | + | + |
| D-Mannose | + | + | + |
| L-Sorbose | − | − | − |
| L-Rhamnose | − | − | − |
| Dulcitol | − | − | − |
| Inositol | − | − | − |
| D-Mannitol | + | + | − |
| D-Sorbitol | + | − | − |
| Methyl-αD-mannoside | − | − | − |
| Methyl-αD-glucoside | + | − | − |
| N-Acetylglucosamine | + | + | + |
| Amygdalin | + | − | − |
| Arbutine | + | + | − |
| Exculine | + | + | − |
| Salicine | + | + | − |
| D-Cellobiose | + | + | − |
| D-Maltose | + | − | − |
| D-Lactose | + | + | + |
| D-Melibiose | − | − | − |
| D-Saccharose(sucrose) | + | − | − |
| D-Trehalose | + | + | − |
| Inulin | − | − | − |
| D-Melezitose | + | + | − |
| D-Raffinose | − | − | − |
| Amidon(starch) | − | − | − |
| Glycogen | − | − | − |
| Xylitol | − | − | − |
| Gentiobiose | + | + | − |
| D-Turanose | + | + | − |
| D-Lyxose | − | − | − |
| D-Tagatose | + | + | + |
| D-Fucose | − | − | − |
| L-Fucose | − | − | − |
| D-Arabitol | − | − | − |
| L-Arabitol | − | − | − |
| Gluconate | W | W | W |
| 2-ketogluconate | − | − | − |
| 5-ketogluconate | − | − | − |
| Number of the isolated strain GMNL-133 matched with the standard strains | | 44 | 34 |

−: negative;
+: positive;
W: weak positive

According to the foregoing results, the isolated strain GMNL-133 is a *Lactobacillus paracasei*.

Example 2

The Difference Analysis of the Isolated *Lactobacillus paracasei* Strain GMNL-133 and Other *Lactobacillus paracasei* Strains in Commercial Products The difference analysis of the isolated *Lactobacillus paracasei* strain GMNL-133 of the present invention and other *Lactobacillus paracasei* strains in commercial yogurts and probiotic health foods was performed. The commercial yogurts were LP33 functional yogurt containing *Lactobacillus paracasei* strain LP33 (for example, Uni-Presiden Co. Ltd., Taiwan) and Otona-no-Genki Yoghurt containing *Lactobacillus paracasei* strain KW3110 (for example, KIRIN holdings Co., Ltd., Japan), and the probiotic health food was Power-Lac sachet containing *Lactobacillus paracasei* strain BRAP-01 (for example, Bio Chain Biotech Co. Ltd., Taiwan). The difference analysis included Random Amplification of Polymorphic DNA (RAPD) PCR analysis and API 50 CHL metabolic profile comparison.

The primer sequence for RAPD PCR analysis was 5'-CCGCGACGTT-3' (SEQ ID No. 2). The PCR procedures were performed in the reaction condition as followed: at 93° C. for 10 minutes to denature double strand DNA to single strand; then at 93° C. for 1 minute, at 36° C. for 1 minute and at 74° C. for 1 minute and this process was repeated 35 cycles; finally the post-extension at 74° C. for 5 minutes. The PCR products were separated by using 1.5% agarose gel electrophoresis and stained with ethidium bromide for typing band patterns.

Figure 2:
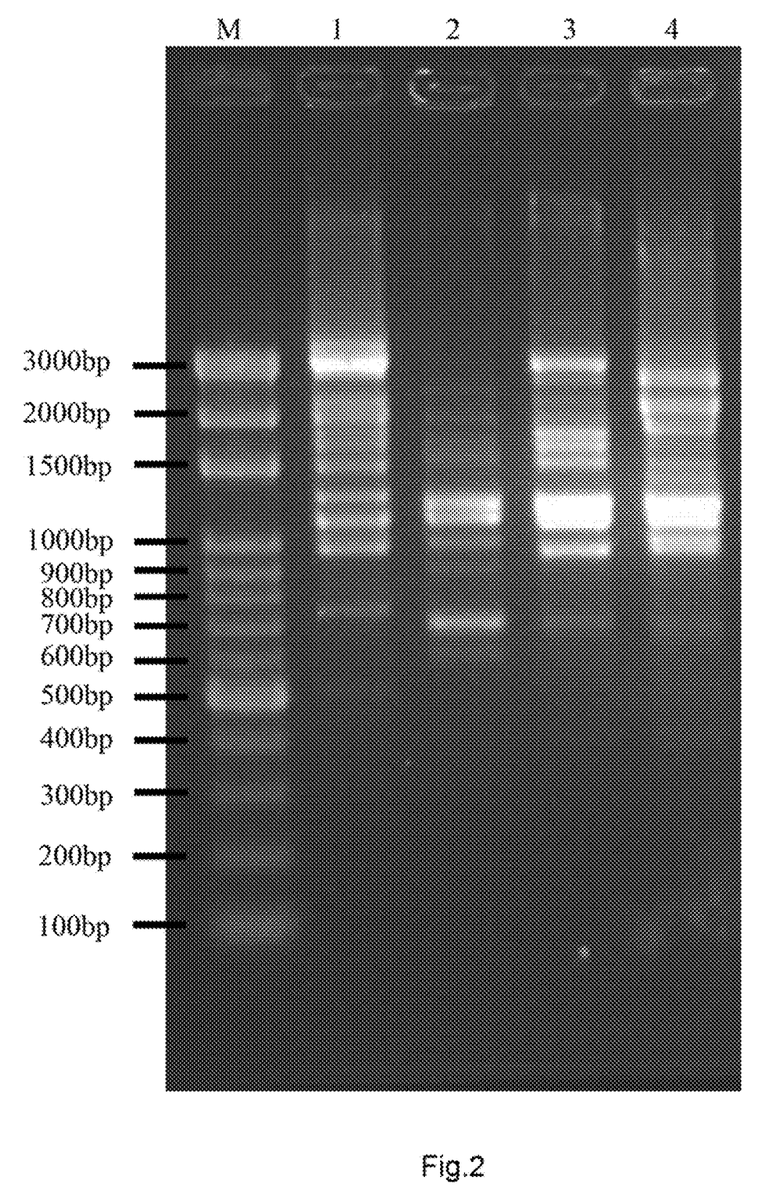
FIG. 2 depicts a RAPD pattern of *Lactobacillus paracasei* strain GMNL-133 and other *Lactobacillus paracasei* strains in commercial products according to an embodiment of the present invention.

FIG. 2 depicts RAPD patterns of *Lactobacillus paracasei* strain GMNL-133 of the present invention and other *Lactobacillus paracasei* strains in commercial products according to an embodiment of the present invention. Lane M is 100 bp ladder maker, and lanes 1 to 4 are RAPD patterns of *Lactobacillus paracasei* strains LP33, KW3110, GMNL-133 and BRAP-01, respectively. According to FIG. 2, the RAPD patterns of *Lactobacillus paracasei* strains LP33, KW3110, GMNL-133 and BRAP-01 are different.

The API 50 CHL metabolic profile of the isolated *Lactobacillus paracasei* strain GMNL-133 of the present invention and that of other *Lactobacillus paracasei* strains in commercial yogurts and probiotic health foods are showed in Table 2.

TABLE 2

| API Test | GMNL-133 | LP33 | BRAP-01 |
| --- | --- | --- | --- |
| Glycerol | − | − | − |
| Erythritol | − | − | − |
| D-Arabinose | − | − | − |
| L-Arabinose | − | − | + |
| D-Ribose | + | + | − |
| D-Xylose | − | − | − |
| L-Xylose | − | − | − |
| D-Adonitol | − | − | − |
| Methyl-βD-xyloside | − | − | + |
| D-Galactose | + | + | + |
| D-Glucose | + | + | + |
| D-Fructose | + | + | + |
| D-Mannose | + | + | + |
| L-Sorbose | − | + | − |
| L-Rhamnose | − | − | + |
| Dulcitol | − | − | − |
| Inositol | − | − | + |
| D-Mannitol | + | + | + |
| D-Sorbitol | + | + | − |
| Methyl-αD-mannoside | − | − | − |
| Methyl-αD-glucoside | + | − | + |
| N-Acetylglucosamine | + | + | + |

TABLE 2-continued

| API Test | GMNL-133 | LP33 | BRAP-01 |
|---|---|---|---|
| Amygdalin | + | − | + |
| Arbutine | + | + | + |
| Exculine | + | + | + |
| Salicine | + | + | + |
| D-Cellobiose | + | + | + |
| D-Maltose | + | + | + |
| D-Lactose | + | + | − |
| D-Melibiose | − | − | + |
| D-Saccharose(sucrose) | + | + | + |
| D-Trehalose | + | + | + |
| Inulin | − | − | + |
| D-Melezitose | + | − | − |
| D-Raffinose | − | − | − |
| Amidon(starch) | − | − | − |
| Glycogen | − | − | − |
| Xylitol | − | − | − |
| Gentiobiose | + | + | + |
| D-Turanose | + | + | − |
| D-Lyxose | − | − | + |
| D-Tagatose | + | + | − |
| D-Fucose | − | − | − |
| L-Fucose | − | − | − |
| D-Arabitol | − | − | − |
| L-Arabitol | − | − | − |
| Gluconate | W | + | − |
| 2-ketogluconate | − | − | − |
| 5-ketogluconate | − | − | − |

−: negative;
+: positive;
W: weak positive

According to the API 50 CHL metabolic profile in Table 2, the metabolisms of the isolated *Lactobacillus paracasei* strain GMNL-133 of the present invention and other commercialized *Lactobacillus paracasei* strains are totally different. For example, *Lactobacillus paracasei* strains GMNL-133 and LP33 do not have exactly the same profile in particular for L-Sorbose, Methyl-αD-glucoside, Amygdalin, and D-Melezitose, and *Lactobacillus paracasei* strains GMNL-133 and BRAP-01 do not have exactly the same profile in particular for L-Arabinose, D-Ribose, Methyl-βD-xyloside, L-Sorbose, L-Rhamnose, Inositol, D-Sorbitol, Methyl-αD-glucoside, Amygdalin, D-Lactose, D-Melibiose, Inulin, D-Tagatose, and Gluconate.

Accordingly, the DNA sequence and the metabolism of *Lactobacillus paracasei* strains GMNL-133, KW3110, LP33 and BRAP-01 are totally different. The isolated *Lactobacillus paracasei* strain GMNL-133 is different from other commercialized *Lactobacillus paracasei* strains, KW3110, LP33, and BRAP-01. Therefore, the isolated *Lactobacillus paracasei* strain GMNL-133 of the present invention is a novel *Lactobacillus paracasei* strain.

Example 3

The Comparison of Secretion Level of Mice Splenocytes Stimulated by the Isolated *Lactobacillus paracasei* Strain GMNL-133 and Other *Lactobacillus paracasei* Strains in Commercial Products The isolated *Lactobacillus paracasei* strain GMNL-133 of the present invention and other *Lactobacillus paracasei* strains KW3110, LP33, BRAP-01 in the foregoing commercial products were respectively co-culture with splenocytes derived from normal mice to compare the IFN-γ secretion level.

The splenocytes derived from BALB/c mice were cultured in RPMI 1640 (GIBCO/BRL®, Gaithersburg, Md., USA) medium containing 10% Fetal bovine serum (FBS). The splenocytes were added into a 96-well plate, which the cell density was adjusted to $4 \times 10^5$ cells per well, and $10^6$ of the foregoing *lactobacillus paracasei* strains were respectively added. The co-culture of the splenocytes and the *Lactobacillus paracasei* strain were incubated under 5% $CO_2$ at 37° C. for 48 hours. Then, the IFN-γ levels of the supernatant of each co-culture sample were determined by commercial ELISA kit (OptEIA Mouse IFN-γ Set, BD Biosciences Pharmingen®, San Diego, Calif., USA).

Figure 3:
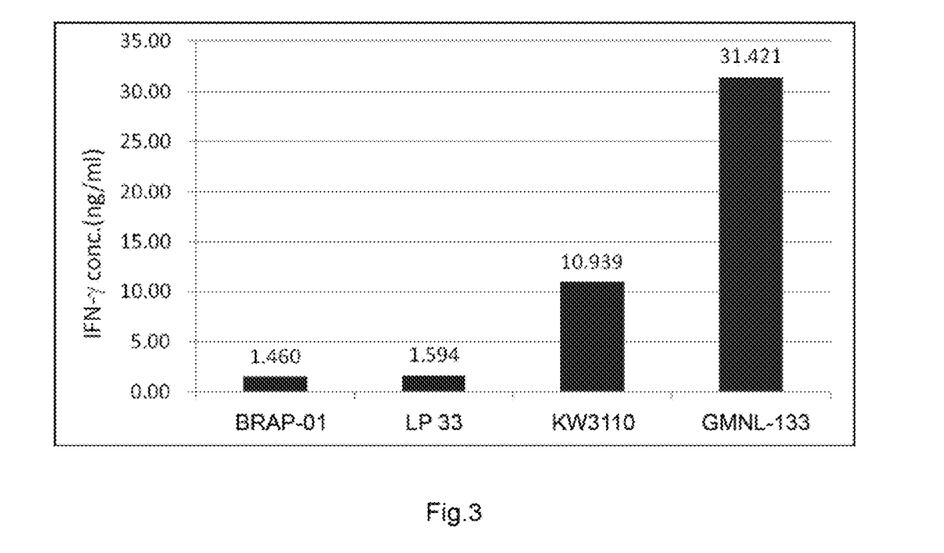
FIG. 3 depicts a bar diagram of IFN-γ expression level in mouse splenocytes after *Lactobacillus paracasei* strain GMNL-133 and other *Lactobacillus paracasei* strains in commercial products treatment according to an embodiment of the present invention.

FIG. 3 depicts a bar diagram of IFN-γ expression level in mouse splenocytes after *Lactobacillus paracasei* strain GMNL-133 and other *Lactobacillus paracasei* strains in commercial products treatment according to an embodiment of the present invention. According FIG. 3, the isolated *Lactobacillus paracasei* strain GMNL-133 could stimulate mouse splenocytes to secret more IFN-γ than other commercialized *Lactobacillus paracasei* strains. Specifically, the IFN-γ secretion level of splenocytes stimulated by the isolated *Lactobacillus paracasei* strain GMNL-133 of the present invention was at least more than 3-fold of that stimulated by the other commercialized *Lactobacillus paracasei* strains. Accordingly, the isolated *Lactobacillus paracasei* strain GMNL-133 of the present invention is more effective in treating allergic disease than other *Lactobacillus paracasei* strains.

Example 4

The Isolated *Lactobacillus paracasei* Strain GMNL-133 for Stimulating the Cytokine Secretion of Allergic Mice Female BALB/c mice were obtained from BioLASCO Taiwan Co., Ltd. and raised for one week in a room where light and temperature were both controlled.

Mice were grouped into Normal Group, Experimental Group, and Placebo Group. The Experimental Group and Placebo Group were actively sensitized by intraperitoneal injection of 50 μg ovalbumin (OVA) with 4 mg aluminum hydroxide adjuvant (alum adjuvant) at day 0. 14 and 28 days after the initial sensitization, the mice were sensitized by intraperitoneal injection of 25 μg OVA with 4 mg aluminum hydroxide adjuvant, again.

The experiment was conducted for 35 days. During the experiment, the Normal Group and the Placebo Group were fed 0.5 ml RO water, and the Experimental Group were fed $2 \times 10^7$ of live *Lactobacillus paracasei* strain GMNL-133 every day from day 1. After the last feeding, 500 μl blood sample was taken from the tail of every mouse, and the mice were sacrificed at day 35. The blood samples were centrifuged to obtain sera for IgE and IgG2a level analysis.

After the mice were sacrificed by $CO_2$ asphyxiation, the spleens were taken to put in a petri dish under sterile environment. 6 ml PBS was added into the petri dish and the spleens were ground with a glass rod to a suspension state. The suspension was slowly added into a 15 ml tube containing 6 ml Ficoll-Hypaque (17-1400-02, Pharmacia), and the splenocytes were separated by gradient centrifugation (720 g for 20 mins). The precipitate was erythrocyte. The splenocytes were taken from the interface and washed by PBS twice. The splenocytes were suspended in RPMI 1640 medium and adjusted to $4 \times 10^6$ cells per ml. 100 μl splenocyte suspension was injected into each well of 96-well plate.

The splenocytes were incubated with 30 μg/ml OVA for 48 hours, and then the TGF-β, IFN-γ, IL-10, and IL-17 level of the supernatants were determined by ELISA.

Figure 4A:
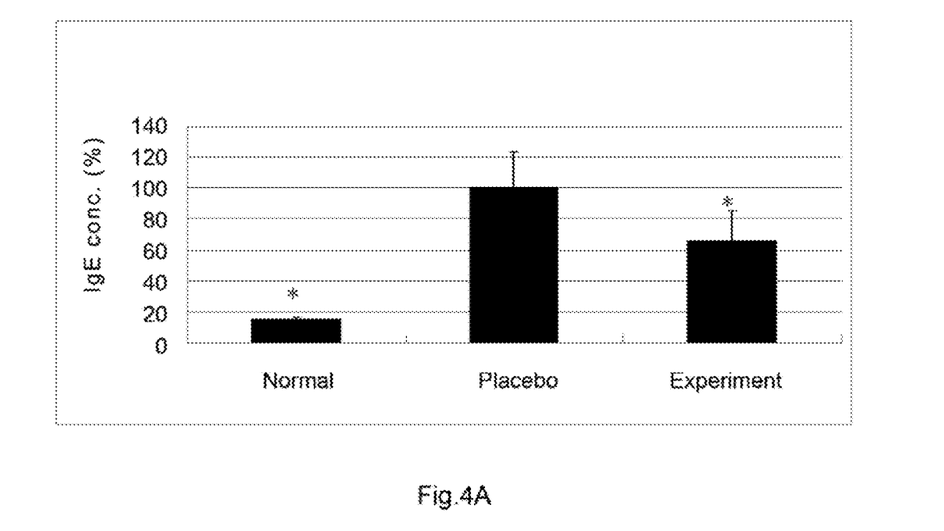
FIG. 4A to 4B depict bar diagrams of relative expression of IgE and IgG2a in serum of each group in allergic mouse model, respectively, which are normalized by IgE and IgG2a of Placebo group, according to an embodiment of the present invention, * is referred to have significant difference between the Experimental and placebo groups (p<0.05)
Figure 4B:
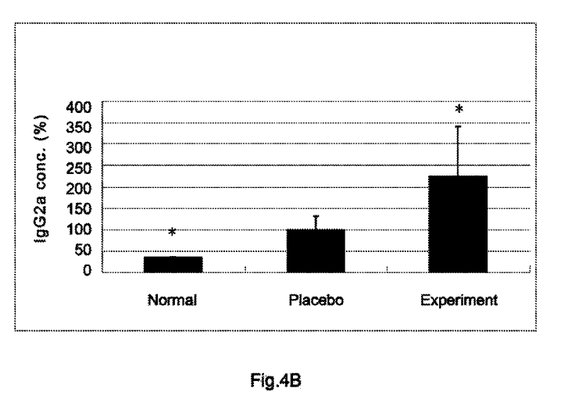
Figure 5A:
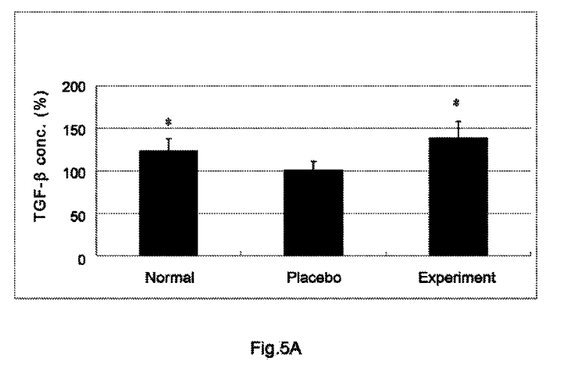
FIG. 5A to 5D depict bar diagrams of relative expression of TGF-β, IFN-γ, IL-10 and IL-17 in spleen cells of each group in allergic mouse model, respectively, which are normalized by TGF-β, IFN-γ, IL-10 and IL-17 of Placebo group, according to an embodiment of the present invention, * is referred to have statistically significant difference between the Experimental and placebo groups (p<0.05)
Figure 5B:
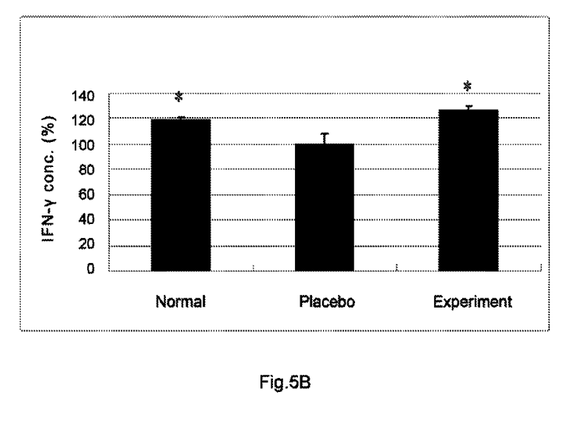
Figure 5C:
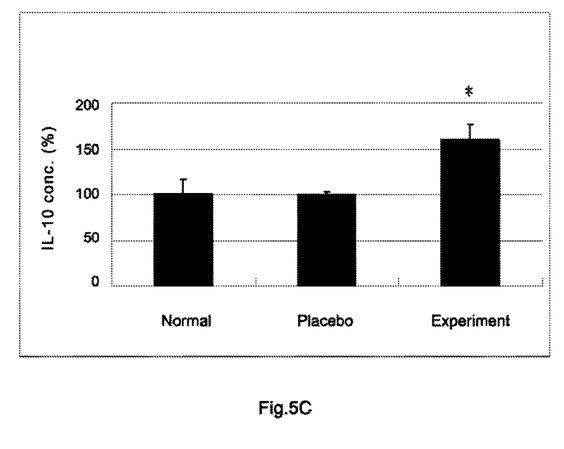
Figure 5D:
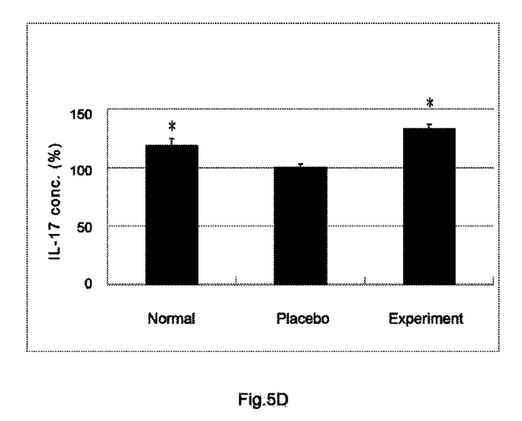

FIG. 4A to 4B depict bar diagrams of relative expression of IgE and IgG2a in serum of each group in allergic mouse model, respectively, which are normalized by IgE and IgG2a of Placebo group, according to an embodiment of the present invention, * is referred to have statistically significant difference between the Experimental and placebo groups (p<0.05). As shown in FIG. 4A and FIG. 4B, compared with the Placebo Group, the OVA specific IgE level in serum of the Experimental Group (*Lactobacillus paracasei* strain GMNL-133 administrated orally) was significantly decreased. However, compared with the Placebo Group, the OVA specific IgG2a level in serum of the Experimental Group (*Lactobacillus paracasei* strain GMNL-133 administrated orally) was significantly increased. According to the literature, IgG2a is secreted by Th1 cells. Therefore, the Th1 cells of BALB/c mice are activated by oral administration of the isolated *Lactobacillus paracasei* strain GMNL-133 to decrease the OVA specific IgE level in sera.

FIG. 5A to 5D depict bar diagrams of relative expression of TGF-β, IFN-γ, IL-10 and IL-17 in splenocytes of each group in allergic mouse model, respectively, which are normalized by TGF-β, IFN-γ, IL-10 and IL-17 of Placebo group, according to an embodiment of the present invention, * is referred to have statistically significant difference between the Experimental and placebo groups (p<0.05). As shown in FIG. 5A to FIG. 5D, compared with the Placebo Group, the TGF-β, IFN-γ, IL-10, and IL-17 levels in supernatant of splenocytes culture of the Experimental Group (*Lactobacillus paracasei* strain GMNL-133 administrated orally) were significantly increased.

Many allergic diseases are caused by the immune response imbalance between the Th1 cells and Th2 cells, and the response to allergens of many allergic diseases tends to Th2 immune response. According to the literature, the allergic diseases could be reduced by improving the balance of Th1/Th2 immune system, and especially by turning the Th2 immune response to the Th1 immune response. When the immune response tends to Th1 immune response pathway, the Th1 cells secret IFN-γ to help the production of IgG2a, the activation of macrophages, nature killer cells, and cytotoxic T cells for enhancing cellular immune response. Moreover, Th17 cells secret IL-17 as a bridge for regulating the innate immunity and the acquired immunity. In other words, Th17 cell is a hub for regulating cell-mediated immunity and humoral immunity.

Furthermore, regulatory T cells could inhibit the allergic diseases by inhibiting the Th2 immune response. The regulatory T cells are characterized as the secretion of IL-10 of TGF-13 for inhibiting the activation and proliferation of the target cells.

In summary, the isolated *Lactobacillus paracasei* strain GMNL-133 of the present invention stimulates the Th17 cells of immune system to turn Th1/Th2 immune system toward Th1 pathway. Furthermore, the isolated *Lactobacillus paracasei* strain GMNL-133 of the present invention also stimulates regulatory T cells and then inhibits Th2 immune response to reduce allergic response.

Example 5

The Effects of Isolated *Lactobacillus paracasei* Strain GMNL-133 in Mouse Atopic Dermatitis Model 6-week old male BALB/c mice for inducing atopic dermatitis were obtained from BioLASCO Taiwan Co., Ltd. and raised for one week in a room where light and temperature were both controlled.

The experiment was conducted for 22 days. Mice were grouped into Normal Group, Placebo Group, and GMNL-133 Group. The GMNL-133 Group and Placebo Group were actively sensitized with 10 ml of 0.3% w/v TNCB solution in acetone applied to the inner site of right ear at day 0. During experiment, 10 µl of 0.3% w/v TNCB solution in acetone was applied to the foregoing same site three times a week to induce atopic dermatitis. During experiment, the Normal Group and the Placebo Group were fed 0.5 ml RO water, and the GMNL-133 Group were fed $2 \times 10^7$ of live *Lactobacillus paracasei* strain GMNL-133 every day through day 1 to day 21.

At day 22, 500 µl blood sample was taken from the tail of every mouse and ear thickness of every mouse was measured with a dial thickness gauge, and then the mice were sacrificed to take mouse right ear tissues. The blood samples were centrifuged to obtain sera for IgE and IgG1 level analysis. The mouse right ear tissues were homogenized in 50 mM phosphate buffer with protease inhibitor (Complete™ protease inhibitor cocktail tablet; Roche Diagnostics, Basel, Switzerland) and then centrifuged for 30 min at 18870×g. Each supernatant was quantified using enzyme-linked immunosorbent assay (ELISA) kit for TNF-α.

Figure 6A:
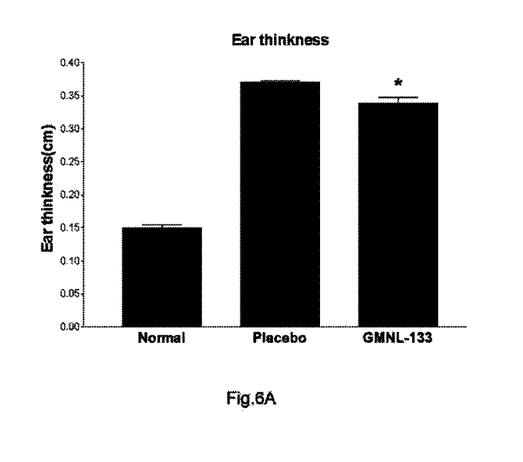
FIG. 6A depicts a bar diagram of right ear thickness of each group in mouse atopic dermatitis model according to an embodiment of the present invention, * is referred to have statistically significant difference between the Experimental and placebo groups (p<0.05)
Figure 6B:
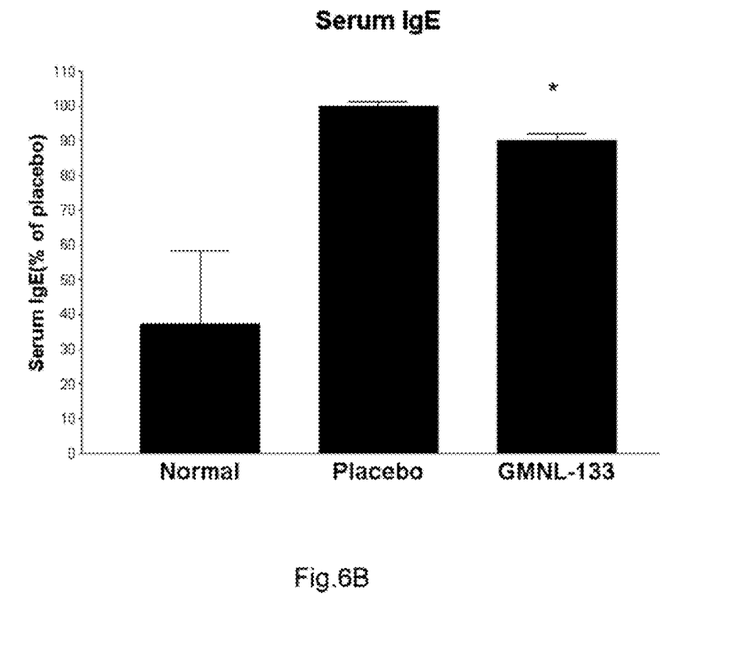
FIG. 6B and FIG. 6C depict bar diagrams of relative expression of serum IgE and IgG1 of each group in mouse atopic dermatitis model, respectively, which are normalized by serum IgE and IgG1 of Placebo group, according to an embodiment of the present invention, * is referred to have statistically significant difference between the Experimental and placebo groups (p<0.05)
Figure 6C:
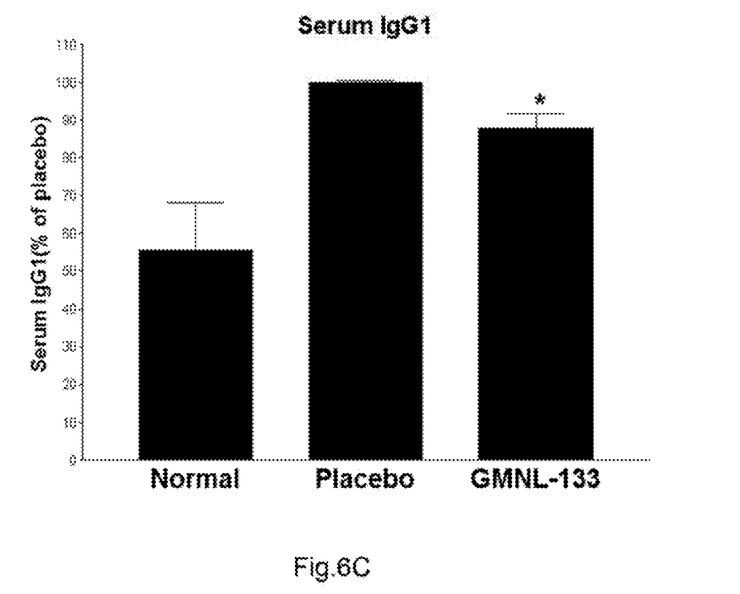
Figure 6D:
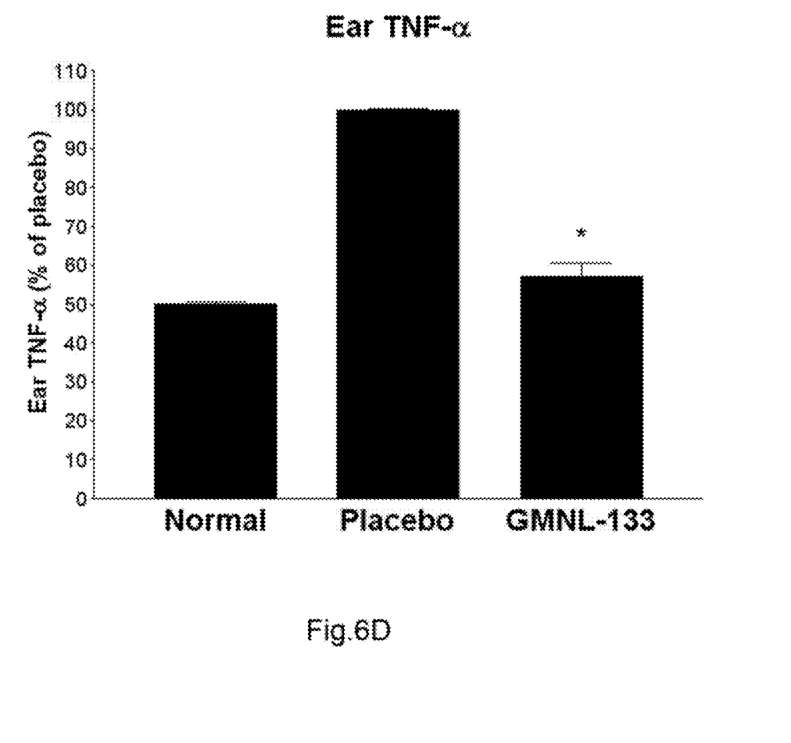
FIG. 6D depicts a bar diagram of relative expression of TNF-α in ear tissues of each group in mouse atopic dermatitis model, which is normalized by TNF-α of Placebo group, according to an embodiment of the present invention, * is referred to have statistically significant difference between the Experimental and placebo groups (p<0.05).

FIG. 6A depicts a bar diagram of right ear thickness of each group in mouse atopic dermatitis model according to an embodiment of the present invention, * is referred to have statistically significant difference between the Experimental and placebo groups (p<0.05). FIG. 6B and FIG. 6C depict bar diagrams of relative expression of serum IgE and IgG1 of each group in mouse atopic dermatitis model, respectively, which are normalized by serum IgE and IgG1 of Placebo group, according to an embodiment of the present invention, * is referred to have statistically significant difference between the Experimental and placebo groups (p<0.05). FIG. 6D depicts a bar diagram of relative expression of TNF-α in ear tissues of each group in mouse atopic dermatitis model, which is normalized by TNF-α of Placebo group, according to an embodiment of the present invention, * is referred to have statistically significant difference between the Experimental and placebo groups (p<0.05).

According to FIG. 6A to FIG. 6D, compared with the Placebo Group, the ear thickness, IgE and IgG1 levels in sera, and TNF-α level in ear tissue of the GMNL-133 Group (*Lactobacillus paracasei* strain GMNL-133 administrated orally) were significantly decreased in mouse atopic dermatitis model. Therefore, the isolated *Lactobacillus paracasei* strain GMNL-133 of the present invention significantly improves the symptoms of atopic dermatitis and also inhibits allergic response in organism.

What is claimed is:

1. An isolated *Lactobacillus paracasei* strain GMNL-133, deposited at the China Center for Type Culture Collection under the accession number of CCTCC M 2011331.

2. A medical composition for treating an atopic dermatitis by oral administration, the medical composition comprising: a therapeutically effective amount of an isolated *Lactobacillus paracasei* strain GMNL-133, which is deposited at the China Center for Type Culture Collection under the accession number of CCTCC M 2011331.

3. The medical composition of claim 2, wherein the isolated *Lactobacillus paracasei* strain GMNL-433 is live.

4. The medical composition of claim 2, further comprising: an another microorganism strain selected from the group consisting of *Lactobacillus acidophilus, Lactobacillus plantarum, Bifidobacterium longum, Lactobacillus fermentum, Lactobacillus bulgaricus, Streptococcus thermophilus, Lactobacillus cremors, Lactobacillus rhamnosus, Lactobacillus reuteri* and any combination thereof.

5. The medical composition of claim 2, further comprising: at least one pharmaceutically acceptable excipient and/or diluent.

* * * * *